US00PP24790P2

(12) United States Plant Patent
Verschoor

(10) Patent No.: US PP24,790 P2
(45) Date of Patent: Aug. 19, 2014

(54) ***PHLOX* PLANT NAMED 'VERSBICOLOR'**

(50) Latin Name: *Phlox paniculata*
Varietal Denomination: Versbicolor

(71) Applicant: Janus Verschoor, Haarlem (NL)

(72) Inventor: Janus Verschoor, Haarlem (NL)

( * ) Notice: Subject to any disclaimer, the term of this patent is extended or adjusted under 35 U.S.C. 154(b) by 0 days.

(21) Appl. No.: 13/694,818

(22) Filed: Jan. 7, 2013

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — Anne Grunberg
(74) *Attorney, Agent, or Firm* — C. A. Whealy

(57) ABSTRACT

A new and distinct cultivar of *Phlox* plant named 'Versbicolor', characterized by its upright and relatively compact plant habit; freely flowering habit; white and pink bi-colored flowers; long flowering period; and good garden performance.

2 Drawing Sheets

Botanical designation: *Phlox paniculata.*
Cultivar denomination: 'VERSBICOLOR'.

BACKGROUND OF THE INVENTION

The present invention relates to a new and distinct cultivar of *Phlox* plant, botanically known as *Phlox paniculata* and hereinafter referred to by the name 'Versbicolor'.

The new *Phlox* plant is a product of a planned breeding program conducted by the Inventor in Haarlem, The Netherlands. The objective of the breeding program was to create new compact and freely-flowering *Phlox* plants with attractive flower coloration.

The new *Phlox* plant originated from a cross-pollination made by the Inventor in 2007 in Haarlem, The Netherlands, of two unnamed seedling selections of *Phlox paniculata*, not patented. The new *Phlox* plant was discovered and selected by the Inventor as a single flowering plant from within the progeny of the stated cross-pollination in a controlled environment in Haarlem, The Netherlands in 2009.

Asexual reproduction of the new *Phlox* plant by cuttings in a controlled environment in Haarlem, The Netherlands since 2009 has shown that the unique features of this new *Phlox* plant are stable and reproduced true to type in successive generations.

SUMMARY OF THE INVENTION

Plants of the new *Phlox* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Versbicolor'. These characteristics in combination distinguish 'Versbicolor' as a new and distinct *Phlox* plant:

1. Upright and relatively compact plant habit.
2. Freely flowering habit.
3. White and pink bi-colored flowers.
4. Long flowering period
5. Good garden performance. .

Plants of the new *Phlox* and the parent selections differ primarily in the following characteristics:

1. Plants of the new *Phlox* are more compact and bushier than plants of the parent selections.
2. Plants of the new *Phlox* are more freely flowering than plants of the parent selections.
3. Plants of the new *Phlox* and the parent selections differ in flower color.

Plants of the new *Phlox* can be compared to plants of the *Phlox paniculata* 'Europa', not patented. In side-by-side comparisons conducted in Haarlem, The Netherlands, plants of the new *Phlox* and 'Europa' differed in the following characteristics:

1. Plants of the new *Phlox* were shorter and more compact than plants of 'Europa'.
2. Plants of the new *Phlox* were more freely flowering than plants of 'Europa'.
3. Plants of the new *Phlox* flowered for a longer period of time than plants of 'Europa'.
4. Plants of the new *Phlox* and 'Europa' differed slightly in flower color.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of typical flowering plants of 'Versbicolor' grown in a container.

The photograph on the second sheet is a close-up view of the upper surface of a typical leaf of 'Versbicolor'.

DETAILED BOTANICAL DESCRIPTION

The aforementioned photographs and following observations, measurements and values describe plants grown in 1.5-liter containers during the late summer/early autumn in an outdoor nursery in Haarlem, The Netherlands and under cultural practices typical of commercial production. During the production of the plants, day temperatures ranged from 16° C. to 32° C. and night temperatures ranged from 6° C. to 18° C. Plants were two years old when the photographs and description were taken. In the following description, color references are made to The Royal Horticultural Society Colour Chart, 2007 Edition, except where general terms of ordinary dictionary significance are used.

Botanical classification: *Phlox paniculata* 'Versbicolor'.

Parentage:

*Female, or seed, parent*.—Unnamed seedling selection of *Phlox paniculata*, not patented.

*Male, or pollen, parent*.—Unnamed seedling selection of *Phlox paniculata*, not patented.

Propagation:

*Type*.—By cuttings.

*Time to initiate roots, summer*.—About three weeks at temperatures about 20° C.

*Time to produce a rooted plant, summer*.—About six weeks at temperatures about 20° C.

*Root description*.—Fine, fibrous; white in color.

*Rooting habit*.—Moderately freely branching; medium density.

Plant description:

*Plant form and growth habit*.—Herbaceous perennial; upright and relatively compact plant habit; broad inverted triangle; low to moderately vigorous growth habit.

*Plant height*.—About 36 cm.

*Plant width* (*spread*).—About 28 cm.

*Lateral branches*.—Length: About 13.1 cm to 28.2 cm. Diameter: About 2.5 mm to 6.5 mm. Internode length: About 3.3 cm. Strength: Strong. Texture: Smooth, glabrous. Color: Close to 144B to 144C.

Foliage description:

*Arrangement*.—Opposite, simple.

*Length*.—About 9.1 cm.

*Width*.—About 3.9 cm.

*Shape*.—Ovate to elliptic.

*Apex*.—Acute.

*Base*.—Truncate.

*Margin*.—Entire.

*Texture, upper and lower surfaces*.—Smooth, glabrous.

*Venation pattern*.—Pinnate.

*Color*.—Developing leaves, upper surface: Close to N137A. Developing leaves, lower surface: Close to 138A. Fully expanded leaves, upper surface: Between 137A and 137D; venation, close to 144B. Fully expanded leaves, lower surface: Between 138B and 147B; venation, close to 144B to 144C.

*Petiole*.—Length: About 3 mm. Diameter: About 4 mm by 2.5 mm. Texture, upper and lower surfaces: Smooth, glabrous. Color, upper and lower surfaces: Close to 144C.

Flower description:

*Flower type and flowering habit*.—Single rotate and salverform flowers arranged in compound terminal panicles; flowers face mostly upright to outwardly; panicles roughly hemispherical in shape; freely flowering habit with about 150 flowers developing per inflorescence.

*Fragrance*.—Moderately fragrant; sweet, pleasant.

*Natural flowering season*.—Plants begin flowering about nine months after planting; long flowering period, plants flower continuously from July through September in The Netherlands.

*Postproduction longevity*.—Flowers last about ten days on the plant; flowers not persistent.

*Flower buds*.—Height: About 2 cm. Diameter: About 5 mm. Shape: Narrowly elliptic to narrowly oblanceolate. Color: Close to N155B flushed with close to 76C to 76D; towards the base, close to 145B to 145C.

*Inflorescence height*.—About 11.3 cm.

*Inflorescence diameter*.—About 11.6 cm.

*Flower diameter*.—About 2.9 cm.

*Flower depth*.—About 2.3 cm.

*Petals*.—Quantity per flower: Typically five in a single whorl; petals fused at the base into a narrow tube. Length: About 2.8 cm. Lobe width: About 1.5 cm. Shape: Spatulate. Apex: Rounded. Margin: Entire. Texture, upper and lower surfaces: Smooth, glabrous; slightly velvety. Color: When opening, upper surface: Close to N155B; towards the base, heavily tinged with between 67B and 68D; throat, close to 150D. When opening, lower surface: Close to N155B; towards the base, tinged with close to 68C; tube, 150D. Fully opened, upper surface: Close to NN155D; towards the base, heavily tinged with close to 68B to 68D; throat, close to 150D. With development, ground color becomes closer to between 76D to N155B; towards the base, tinged with close to 75A to 75C; throat, between 150D and 157C. Fully opened, lower surface: Close to NN155D; towards the base, tinged with close to 75B to 75D; tube, 150D.

*Sepals*.—Quantity per flower: Typically five in a single whorl, fused towards the base; calyx, campanulate. Length: About 9 mm. Width: About 2 mm. Shape: Lanceolate. Apex: Narrowly apiculate. Margin: Entire. Texture, upper and lower surfaces: Smooth, glabrous. Color: When opening, upper and lower surfaces: Close to 144A; towards the base, close to 144C; towards the margins, close to 145D. Fully opened, upper and lower surfaces: Close to 144A; towards the base, close to 144C; towards the margins, close to 145D.

*Peduncles*.—Length: About 7.5 cm. Diameter: About 2.5 mm. Angle: Main peduncle, erect; lateral peduncles, about 40° from vertical. Strength: Strong. Texture: Smooth, glabrous. Color: Close to 145B.

*Pedicels*.—Length: About 4 mm. Diameter: About 1 mm. Angle: About 30° from the peduncle axis. Strength: Strong. Texture: Smooth, glabrous. Color: Close to 145B.

*Reproductive organs*.—Stamens: Quantity per flower: Typically five; filaments fused with petals. Filament length: About 1 mm. Filament color: Close to 145B. Anther length: About 2 mm. Anther shape: Oblong. Anther color: Close to 12B to 12C. Pollen amount: Medium. Pollen color: Close to 11D. Pistils: Quantity per flower: One. Pistil length: About 1.2 cm. Stigma shape: Three-parted. Stigma color: Close to 145D. Style length: About 1.1 cm. Style color: Close to 145C. Ovary color: Close to 143B.

*Seeds and fruits*.—Seed and fruit development have not been observed on plants of the new *Phlox*.

Disease & pest resistance: Plants of the new *Phlox* have been observed to be relatively tolerant to Powdery Mildew. Plants of the new *Phlox* have not been noted to be resistant to pests and other pathogens common to *Phlox* plants.

Garden performance: Plants of the new *Phlox* have been observed to have good garden performance and tolerate rain, wind, high temperatures about 35° C. and to be winter hardy to USDA Hardiness Zone 6.

It is claimed:

1. A new and distinct *Phlox* plant named 'Versbicolor' as illustrated and described.

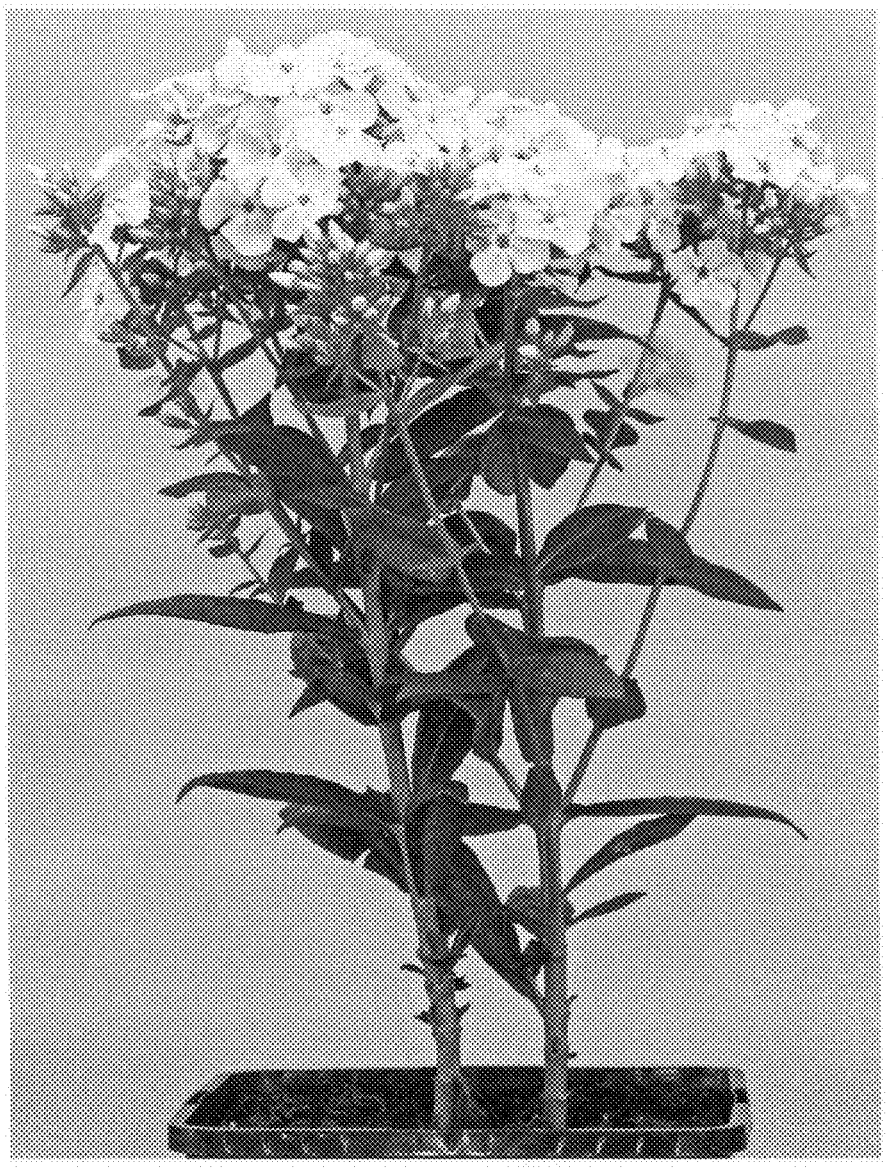

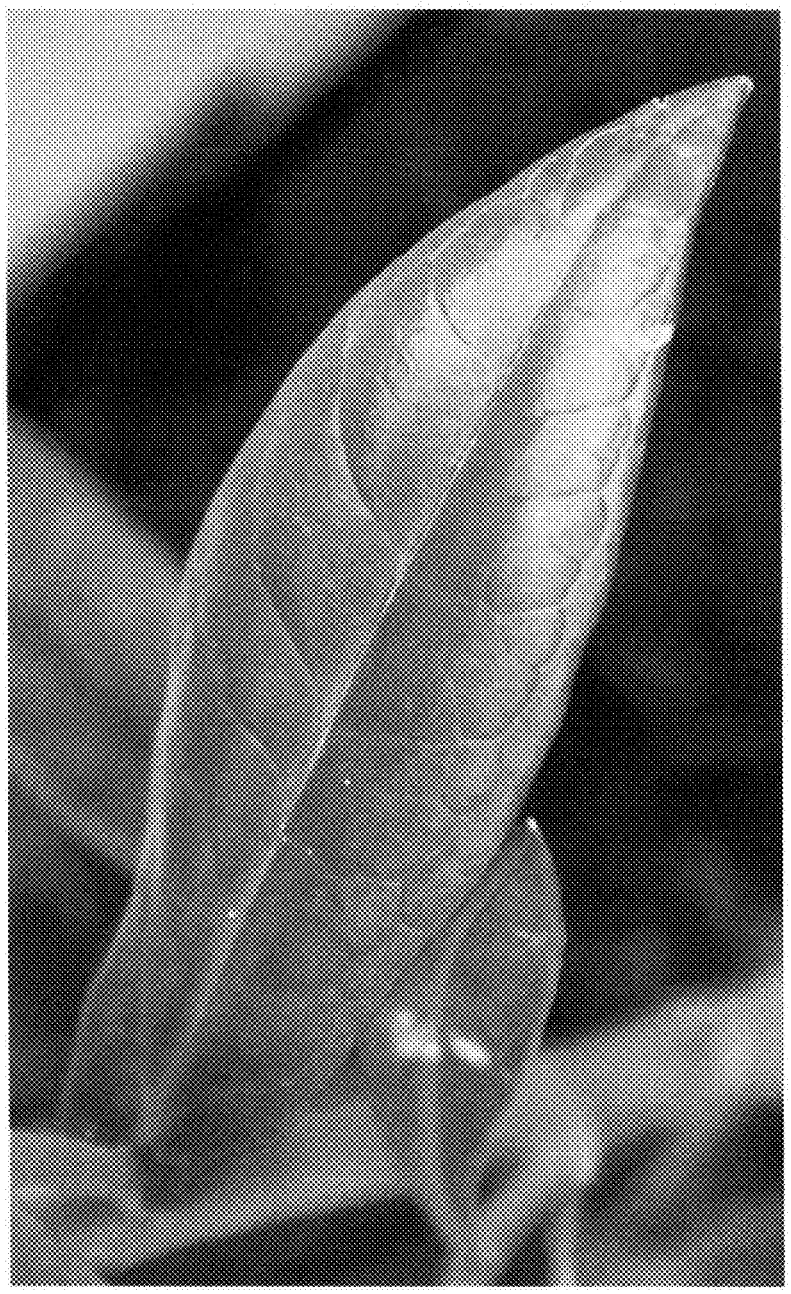

* * * * *